(12) United States Patent
Li et al.

(10) Patent No.: US 7,576,086 B2
(45) Date of Patent: Aug. 18, 2009

(54) ARALKYL-ALCOHOL PEIPERAZINE DERIVATIVES AND THEIR USES AS ANTIDEPRESSANT

(75) Inventors: Jianqi Li, Shanghai (CN); Liying Huang, Shanghai (CN); Wenxin Dong, Shanghai (CN); Xia Ge, Shanghai (CN); Chengjin Shi, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 432 days.

(21) Appl. No.: 10/516,205

(22) PCT Filed: Apr. 16, 2003

(86) PCT No.: PCT/CN03/00275

§ 371 (c)(1),
(2), (4) Date: Dec. 1, 2004

(87) PCT Pub. No.: WO03/101974

PCT Pub. Date: Dec. 11, 2003

(65) Prior Publication Data

US 2005/0267121 A1    Dec. 1, 2005

(30) Foreign Application Priority Data

Jun. 3, 2002    (CN)    ............... 02 1 11934

(51) Int. Cl.
*A61K 31/497*    (2006.01)
*A61K 31/4965*    (2006.01)
*C07D 241/04*    (2006.01)
*C07D 295/00*    (2006.01)
*C07D 401/00*    (2006.01)
*C07D 403/00*    (2006.01)
*C07D 405/00*    (2006.01)
*C07D 409/00*    (2006.01)
*C07D 411/00*    (2006.01)

(52) U.S. Cl. ............ 514/252.13; 514/255.01; 514/255.05; 544/358; 544/360; 544/363; 544/364; 544/377

(58) Field of Classification Search ............ 514/252.13, 514/255.01, 255.05; 544/358, 377, 363, 544/360, 364
See application file for complete search history.

(56) References Cited

U.S. PATENT DOCUMENTS 6,395,739 B1 *    5/2002    Sato et al. ............... 514/254.09

FOREIGN PATENT DOCUMENTS

| CN | 87100652 |   | 8/1987 |
|---|---|---|---|
| CN | 1128026 |   | 7/1996 |
| CN | 1187128 |   | 7/1998 |
| CN | 1230180 |   | 9/1999 |
| JP | 10203986 | * | 8/1998 |
| WO | WO 0250061 | * | 6/2002 |

OTHER PUBLICATIONS

Lutz, R., et al., Antimarlarials. Some Piperazine Derivatives, Journal of Organic Chemistry, 12, 771-5 (1947).*
Baltzly, R., et al., Preparation of N-monosubstituted and unsymmetrically disubstituted piperazines, Journal of the American Chemical Society, 66, 263-6 (1944).*
Kaufmann, et al., Multiresidue Analysis of Tranquilizers and the Beta-blocker Carazolyl in Meat by Liquid Chromotography/tandem Mass Spectrometry, Rapid Communications in Mass Spectrometry 15(18), 1747-1751 (2001).*

* cited by examiner

*Primary Examiner*—James O Wilson
*Assistant Examiner*—Erich A Leeser
(74) *Attorney, Agent, or Firm*—Crowell & Moring LLP

(57) ABSTRACT

Aryl alkanol piperazine derivatives of the formula $$Ar_1-(CH)n-N\underset{R_1}{\overset{1}{\diagup}}\underset{}{\overset{4}{\diagdown}}N-(CH)m-\underset{H}{\overset{OH}{\underset{|}{C}}}-Ar_2$$

and pharmaceutical compositions comprising the same. Also disclosed are methods for treating depression using the pharmaceutical composition. Compounds of the invention have excellent dual inhibitory actions to the uptake of the monoamines neurotransmitter, good antidepressant activities and minor side effects.

11 Claims, No Drawings

ARALKYL-ALCOHOL PEIPERAZINE DERIVATIVES AND THEIR USES AS ANTIDEPRESSANT

FIELD OF INVENTION

The present invention relates to aryl alkanol piperazine derivatives and their applications as antidepressants.

TECHNICAL BACKGROUND

Depression is one of the most common mental diseases. The incidence of this disease is about 5% of the world's population and it seriously affects our health and daily life. It is predicted that by 2020, depression will become the second most deadly illness that bothers our well-being and shortens our life span (second only to ischemic heart diseases.)

Although many antidepressants have been used clinically, many patients still suffer from depression after treatment because of the poor efficacy and latent side effects of some drugs. For many patients, electricity convulsion treatment remains necessary. Therefore, the development of antidepressants is definitely among the top popular topics in new medicine research. Many pharmaceutical companies invest massive funds into developing better antidepressants. The pathogenesis of depression is unknown, but is thought to be related to transmission impediment of 5-Hydroxytryptamine (5-HT) and noradrenalin (NA) at synapses in the brain. Taking this point into consideration, the research of antidepressants usually focuses on enhancing the transmission function of NA and 5-HT at synapses in the brain. Due to many side effects of traditional TCA antidepressants, it will eventually be replaced by selective serotonin-reuptake inhibitors (SSRI) and other new generations of antidepressants. In the past 20 years, the appearance of SSRI, represented by fluoxetine, made a big progress in the treatment of depression. The main advantages of this kind of antidepressants are fewer side effects, convenient administration, -- and better tolerance; therefore, it is usually chosen as the first-line treatment to most patients suffering from depression. Reboxetine, which was marketed for the first time in 1997 in the United Kingdom, is the first drug of selective Norepinephrine-reuptake Inhibitors (NARI). This drug has better tolerance and better effects than SSRI in the treatment of depression. Another kind of new medicine is NA and specific 5-HT antidepressants such as Mirtazapine and Mianserine. These medicines involve both serotonergic and noradrenergic enhancement through blockade of the α2-autoreceptor and α2-heteroreceptor, increasing the release of NA and 5-HT in the synapses. American Home Products, Inc. (AHP) released a new antidepressant drug under the tradename Venlafaxine in 1997, which is the first one that is capable of inhibiting both NA and 5-HT reuptake (SNRI). Its characteristic is its rapid pharmacodynamic response. This is significant because slow response is seen as concern in other modern antidepressants. Venlafaxine has shown to be effective at treating severe and chronical depression. Compared with SSRI, the understanding of the SNRI compounds is limited.

Although different types of antidepressants have their own merits, it seems that there is no such drug that is particularly effective. Improvement is only made on their tolerance; and most of them have strong inhibitory actions to the cytochrome P450 system. Therefore, the antidepressants on the market today still cannot satisfy the need of treating depression. Many companies are studying different 5-HT subtype acceptor inhibitors. In addition, the launch of dual-acting antidepressants have prompted efforts to develop new antidepressants having triple actions on 5-HT, NA and DA systems.

DESCRIPTION OF THE INVENTION

The first aspect of the present invention provides aryl alkanol piperazine derivatives that overcome the defects of the existing antidepressants, such as insufficient antidepressant activity and strong antagonism to the cytochrome P450 system, to satisfy the needs of depression treatment.

The second aspect of the present invention provides methods of using the above compounds as antidepressants.

The aryl alkanol piperazine derivatives described in the present invention are free base or salts of the compounds represented by the following general formula:

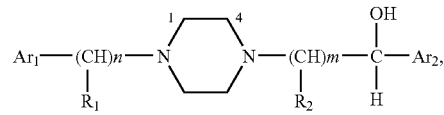

in which the salts are one of hydrochloride, hydrobromide, sulfate, trifluoroacetate or methanesulfonate etc. Preferably the salt is hydrochloride or hydrobromide, and can contain about 0.5-3 molecules of hydrate water.

Wherein $Ar_1$ and $Ar_2$ independently represent:

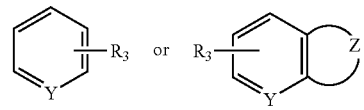

each of $R_1$, $R_2$ and $R_3$ can represent any one of hydrogen, a $C_1$-$C_3$ alkyl group, a $C_5$ or $C_6$ cycloalkyl group, a phenyl, substituted phenyl, hydroxyl, methoxy, ethoxy, amino, substituted amino, halogen, carboxylic, carboxylic ester, nitryl or acetonitrile group.

$R_1$, $R_2$ and $R_3$ preferably represent one of hydrogen, a $C_1$-$C_3$ alkyl group, a hydroxyl, methoxy, ethoxy, amino, substituted amino, halogen or nitryl group.

Y represents one of C, N, or O.

Z represents a five or six-member ring containing at least one of C, S, N or O; and n=0, 1, 2, 3; m=1, 2, 3.

The unsymmetrical carbons of the structure may be achiral carbon atoms or chiral ones.

The preferable compounds are as follows:

IV-1  $N^1$-benzyl-$N^4$-(phenylpropane-2-yl-3-ol)piperazine,
IV-2  $N^1$-(4-chlorobenzyl)-$N^4$-(phenylpropane-2-yl-3-ol)piperazine,
IV-3  $N^1$-(1-phenylethyl)-$N^4$-(phenylpropane-2-yl-3-ol)piperazine,
IV-4  $N^1$-benzyl-$N^4$-[2-(4-chlorophenyl)ethyl-2-ol]piperazine,
IV-5  $N^1$-(3-pyridylmethyl)-$N^4$-(2-phenylethyl-2-ol)piperazine,
IV-6  $N^1$-(4-fluorobenzyl)-$N^4$-(2-phenylethyl-2-ol)piperazine,
IV-7  $N^1$-benzyl-$N^4$-[2-(4-nitrophenyl)ethyl-2-ol]piperazine,
IV-8  $N^1$-benzyl-$N^4$-[(1,2-diphenyl)ethyl-2-ol]piperazine,
IV-9  $N^1$-(4-nitrobenzyl)-$N^4$-[2-(4-acetamidophenyl)ethyl-2-ol]piperazine,
IV-10 $N^1$-benzyl-$N^4$-[2-(4-acetamidophenyl)ethyl-2-ol]piperazine,
IV-11 $N^1$-(4-fluorobenzyl)-$N^4$-[2-(4-chlorophenyl)ethyl-2-ol]piperazine,
IV-12 $N^1$-[1-(4-nitrophenyl)ethyl]-$N^4$-(2-phenylethyl-2-ol)piperazine,
IV-13 $N^1$-(3-methoxybenzyl)-$N^4$-(2-phenylethyl-2-ol)piperazine, -continued IV-14 N$^1$-(2-nitro-5-methoxybenzyl)-N$^4$-(2-phenylethyl-2-ol)piperazine,
IV-15 N$^1$-[1-(4-nitrophenyl)ethyl]-N$^4$-[2-(4-methylphenyl)ethyl-2-ol]piperazine,
IV-16 N$^1$-benzyl-N$^4$-[2-(5-chloro-6-methoxy-2-naphthyl)ethyl-2-ol]piperazine,
IV-17 N1-(3-chlorophenyl)-N4-[1-(5-chloro-6-methoxyl-naphthalen-2-yl)-propane-2-yl-1-ol]piperazine,
IV-18 N1-(2-phenylethyl-2-ol)-N4-[1-(5-chloro-6-methoxyl-naphthalen-2-yl)-propane-2-yl-1-ol]piperazine,
IV-19 N1-benzyl-N4-[1-(5-chloro-6-methoxyl-naphthalen-2-yl)-propane-2-yl-1-ol]piperazine,
IV-20 N1-(4-nitrobenzyl)-N4-[1-(5-chloro-6-methoxyl-naphthalen-2-yl)-propane-2-yl-1-ol]piperazine,
IV-21 N1-(4-aminobenzyl)-N4-[1-(5-chloro-6-methoxyl-naphthalen-2-yl)-propane-2-yl-1-ol]piperazine,
IV-22 N$^1$-(3,4,5-trimethoxybenzyl)-N4-[1-(5-chloro-6-methoxyl-naphthalen-2-yl)-propane-2-yl-1-ol]piperazine,
IV-23 N$^1$-(4-methoxybenzyl)-N$^4$-(2-phenylethyl-2-ol)piperazine,
IV-24 N$^1$-(4-methoxybenzyl)-N$^4$-(S-2-phenylethyl-2-ol)piperazine,
IV-25 N$^1$-(4-methoxybenzyl)-N$^4$-(R-2-phenylethyl-2-ol)piperazine,
IV-26 N$^1$-(4-nitrobenzyl)-N$^4$-(2-phenylethyl-2-ol)piperazine,
IV-27 N$^1$-(4-nitrobenzyl)-N$^4$-(S-2-phenylethyl-2-ol)piperazine,
IV-28 N$^1$-(4-nitrobenzyl)-N$^4$-(R-2-phenylethyl-2-ol)piperazine,
IV-29 N$^1$-(1-phenylethyl)-N$^4$-(2-phenylethyl-2-ol)piperazine,
IV-30 N$^1$-(R-1-phenylethyl)-N$^4$-(R-2-phenylethyl-2-ol)piperazine,
IV-31 N$^1$-(R-1-phenylethyl)-N$^4$-(S-2-phenylethyl-2-ol)piperazine,
IV-32 N$^1$-(S-1-phenylethyl)-N$^4$-(S-2-phenylethyl-2-ol)piperazine,
IV-33 N$^1$-(S-1-phenylethyl)-N$^4$-R-2-phenylethyl-2-ol)piperazine,
IV-34 N$^1$-(S-1-phenylethyl)-N$^4$-[1-(5-chloro-6-methoxyl-naphthalen-2-yl)-propane-2-yl-1-ol]piperazine,
IV-35 N$^1$-(R-1-phenylethyl)-N$^4$-[1-(5-chloro-6-methoxyl-naphthalen-2-yl)-propane-2-yl-1-ol]piperazine,
IV-36 N$^1$-benzyl-N$^4$-(2-phenylethyl-2-ol)piperazine,
IV-37 N$^1$-(4-chlorobenzyl)-N$^4$-(2-phenylethyl-2-ol)piperazine,
IV-38 N$^1$-(4-chlorobenzyl)-N$^4$-[2-(4-chlorophenyl)ethyl-2-ol]piperazine,
IV-39 N$^1$-benzyl-N$^4$-[2-(4-methoxyphenyl)ethyl-2-ol]piperazine,
IV-40 N$^1$,N$^4$-di(2-phenylethyl-2-ol)-piperazine,
IV-41 N$^1$-(4-a minobenzyl)-N$^4$-(2-phenylethyl-2-ol)piperazine,
IV-42 N$^1$-benzyl-N$^4$-[(2-naphthyl) ethyl-2-ol]piperazine,
IV-43 N$^1$-benzyl-N$^4$-[(3-phenyl)propyl-3-ol]piperazine,
IV-44 N$^1$-(2,4-dimethoxybenzyl)-N$^4$-(2-phenylethyl-2-ol)piperazine,
IV-45 N$^1$-benzyl-N$^4$-(S-2-phenylethyl-2-ol)piperazine,
IV-46 N$^1$-benzyl-N$^4$-(R-2-phenylethyl-2-ol)piperazine,
IV-47 N$^1$-(1-phenylpropyl)-N$^4$-(2-phenylethyl-2-ol)piperazine,
IV-48 N$^1$-(4-fluorobenzyl)-N$^4$-(2-phenylethyl-2-ol)piperazine,
IV-49 N$^1$-(3,4-methylenedioxybenzyl)-N$^4$-(2-phenylethyl-2-ol)piperazine,
IV-50 N$^1$-(1-phenethyl)-N$^4$-[2-(4-methylphenyl)ethyl-2-ol]piperazine,
IV-51 N$^1$-(S-1-phenylethyl)-N$^4$-[2-(4-methylphenyl)ethyl-2-ol]piperazine,
IV-52 N$^1$-(R-1-phenethyl)-N$^4$-[2-(4-methylphenyl)ethyl-2-ol]piperazine.

A preferable compound is IV-19 N$^1$-benzyl-N$^4$-[1-(5-chloro-6-methoxyl-naphthalen-2-yl)-propane-2-yl-1-ol] piperazine.

Their structures are shown in Table 1

TABLE 1

| Code | Ar$_1$ | Ar$_2$ | R$_1$ | R$_2$ | n | m |
|---|---|---|---|---|---|---|
| IV-1 | Ph | Ph | H | CH$_3$ | 1 | 1 |
| IV-2 | 4-Cl-C$_6$H$_4$- | Ph | H | CH$_3$ | 1 | 1 |
| IV-3 | Ph | Ph | CH$_3$ | CH$_3$ | 1 | 1 |
| IV-4 | Ph | 4-Cl-C$_6$H$_4$- | H | H | 1 | 1 |
| IV-5 | 3-pyridyl | Ph | H | H | 1 | 1 |
| IV-6 | 4-F-C$_6$H$_4$- | Ph | H | H | 1 | 1 |
| IV-7 | Ph | 4-NO$_2$-C$_6$H$_4$- | H | H | 1 | 1 |
| IV-8 | Ph | Ph | H | Ph | 1 | 1 |
| IV-9 | 4-NO$_2$-C$_6$H$_4$- | 4-NHCOCH$_3$-C$_6$H$_4$- | H | H | 1 | 1 |
| IV-10 | Ph | 4-NHCOCH$_3$-C$_6$H$_4$- | H | H | 1 | 1 |

TABLE 1-continued

| Code | Ar₁ | Ar₂ | R₁ | R₂ | n | m |
|---|---|---|---|---|---|---|
| IV-11 | 4-F-C₆H₄ | 4-Cl-C₆H₄ | H | H | 1 | 1 |
| IV-12 | 4-NO₂-C₆H₄ | Ph | CH₃ | H | 1 | 1 |
| IV-13 | 3-CH₃O-C₆H₄ | Ph | H | H | 1 | 1 |
| IV-14 | 4-CH₃O-3-NO₂-C₆H₃ | Ph | H | H | 1 | 1 |
| IV-15 | 4-NO₂-C₆H₄ | 4-CH₃-C₆H₄ | CH₃ | H | 1 | 1 |
| IV-16 | Ph | 1-Cl-2-CH₃O-6-methyl-naphthyl | H | H | 1 | 1 |
| IV-17 | 4-Cl-C₆H₄ | 1-Cl-2-CH₃O-6-methyl-naphthyl | 0 | CH₃ | 0 | 1 |
| IV-18 | Ph-CH(OH)-CH₃ | 1-Cl-2-CH₃O-6-methyl-naphthyl | H | CH₃ | 1 | 1 |
| IV-19 | Ph | 1-Cl-2-CH₃O-6-methyl-naphthyl | H | CH₃ | 1 | 1 |
| IV-20 | 4-NO₂-C₆H₄ | 1-Cl-2-CH₃O-6-methyl-naphthyl | H | CH₃ | 1 | 1 |
| IV-21 | 4-H₂N-C₆H₄ | 1-Cl-2-CH₃O-6-methyl-naphthyl | H | CH₃ | 1 | 1 |

TABLE 1-continued

| Code | Ar₁ | Ar₂ | R₁ | R₂ | n | m |
|---|---|---|---|---|---|---|
| IV-22 | 3,4,5-tri(CH₃O)-C₆H₂- | 1-Cl-2-CH₃O-6-methyl-naphthalen-yl | H | CH₃ | 1 | 1 |
| IV-23* | 4-CH₃O-C₆H₄- | Ph | H | H | 1 | 1 |
| IV-26* | 4-NO₂-C₆H₄- | Ph | H | H | 1 | 1 |
| IV-29* | Ph | Ph | CH₃ | H | 1 | 1 |
| IV-34 | Ph | 1-Cl-2-CH₃O-6-methyl-naphthalen-yl | (S)CH₃ | CH₃ | 1 | 1 |
| IV-35 | Ph | 1-Cl-2-CH₃O-6-methyl-naphthalen-yl | (R)CH₃ | CH₃ | 1 | 1 |
| IV-36 | Ph | Ph | H | H | 1 | 1 |
| IV-37 | 4-Cl-C₆H₄- | Ph | H | H | 1 | 1 |
| IV-38 | 4-Cl-C₆H₄- | 4-Cl-C₆H₄- | H | H | 1 | 1 |
| IV-39 | Ph | 4-CH₃O-C₆H₄- | H | H | 1 | 1 |
| IV-40 | C₆H₅-CH(OH)- | Ph | H | H | 1 | 1 |
| IV-41 | 4-H₂N-C₆H₄- | Ph | H | H | 1 | 1 |
| IV-42 | Ph | 6-methyl-naphthalen-2-yl | H | H | 1 | 1 |
| IV-43 | Ph | Ph | H | H | 1 | 2 |
| IV-44 | 2,5-di(CH₃O)-C₆H₃- (with OC) | Ph | H | H | 1 | 1 |

TABLE 1-continued

| Code | Ar₁ | Ar₂ | R₁ | R₂ | n | m |
|---|---|---|---|---|---|---|
| IV-45* | Ph | Ph | H | H | 1 | 1 |
| IV-47 | Ph | Ph | CH₂CH₃ | H | 1 | 1 |
| IV-48 | 4-F-C₆H₄ | Ph | H | H | 1 | 1 |
| IV-49 | 3,4-methylenedioxyphenyl | Ph | H | H | 1 | 1 |
| IV-50* | Ph | 4-CH₃-C₆H₄ | CH₃ | H | 1 | 1 |

*a racemic compound and its corresponding optical isomers

The compounds in this invention can be prepared as follows:

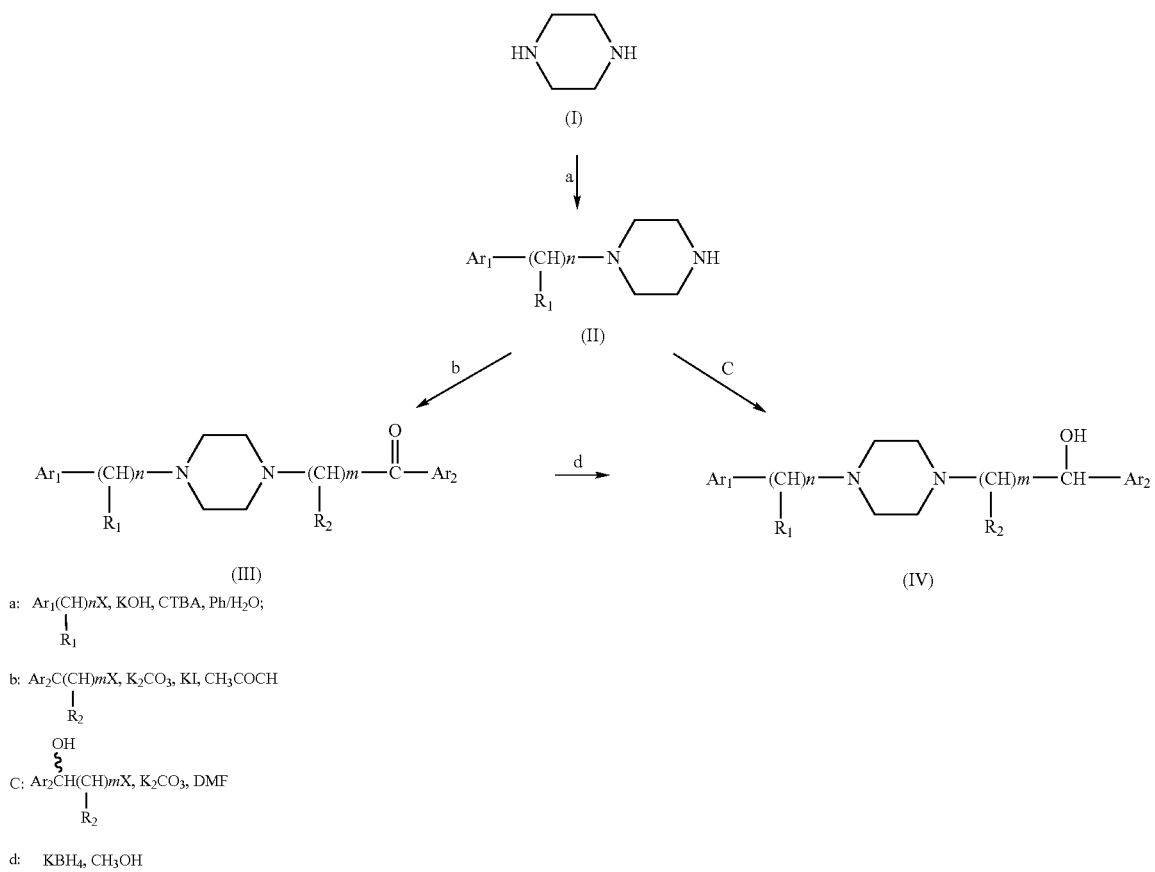

a: Ar₁(CH)$n$X, KOH, CTBA, Ph/H₂O;
   |
   R₁ b: Ar₂C(CH)$m$X, K₂CO₃, KI, CH₃COCH
   |
   R₂ c: Ar₂CH(CH)$m$X, K₂CO₃, DMF
   |  |
   OH R₂ d: KBH₄, CH₃OH

Piperazine is used as a starting material to prepare the above-mentioned compounds. First, piperazine is reacted with the corresponding halogenated arylalkane through the nucleophilic substitution reaction using phase transfer catalysis to produce the N-monoalkylated compound (II). The reaction is carried out using hexadecyl trimethyl bromoa mine (CTAB) as a phase transfer catalyst, benzene/water is the solvent system, and KOH for alkylation on one N atom of the piperazine ring, with a yield of 86%.

Compound (II) is alkylated at N⁴ with the corresponding halogenated aralkylketone through the hydrocarbylation reaction to obtain the aralkylketone piperazine (III). When using $K_2CO_3$/DMF, the reaction can take place at room temperature, and the yield is about 80%. If using $K_2CO_3$/$CH_3COCH_3$, $NaHCO_3$/$C_2H_5OH$ or $Et_3N$/$CHCl_3$ as reaction systems, it needs reflux for 8-24 h, the color of reaction will darken as time passes, and prolonged reaction will reduce the quality and yield of the products. The main intermediate (III) can be obtained by the above mentioned processes.

Finally, the compound (III) is reduced with $KBH_4$ in $CH_3OH$ under reflux for 3-5 hours to give the corresponding aryl alkanol piperazine compound (IV), which also can be prepared directly from compound (II) by step c. The goal compounds IV-1 to IV-52 are obtained by the above mentioned procedures.

The halogenated arylalkane and the halogenated arylformoxylalkyl compounds in steps a, b and c can be obtained commercially, and also be prepared by using bro mine or copper bromide with corresponding aralkyl ketones according to published conventional methods.

The aryl alkanol piperazine derivatives described in this invention have dual inhibitory actions on 5-HT and NA reuptake, and they can be used as antidepressant.

Pharmaceutical compositions comprising the derivatives described in this invention can be ad ministered to depression patients orally or via injection and so on.

The pharmaceutical composition may comprise an effective amount of a compound of the invention with one or more pharmaceutically acceptable carriers.

The carriers mentioned above include dilutents, excipients (water, etc), adhesives (fibrin derivatives, gelation, polyvinyl, pyrrolidone, etc), filling materials (starch, etc), disitegrants (calcium carbonate, sodium bicarbonate, etc) and other auxiliary materials like flavor and edulcorant.

For oral administration, the compounds can be prepared as solid formulations, such as tablets, powders or capsules. For injection, they can be prepared as a liquid form.

Each formulation of the compositions in this invention may be prepared by pharmaceutically conventional methods, and the content of the active compound may be 0.1-99.5%.

The dosage of the compounds could be regulated according to various taking methods, the age and the weight of patients, and specific cases of diseases. Daily whole dosage can be 5-30 mg/kg (po) or 1-10 mg/kg (iv).

The derivatives in this invention demonstrated the antagonism to depression in the animal trials.

The inventors discover that derivatives of the present invention have a broader indication, a smaller side effect, a lower toxicity, and a slighter nerve side effect than the single action mechanism antidepressants used clinically at present like Desipra mine and Fluoxetine.

EXAMPLES

General Preparation 1: N-aralkyl piperazine dihydrochloride (II)

A mixture of piperazine hexahydrate (350 mmol), solid KOH (100 mmol) and CTAB (Hexadecyl Trimethylammonium Bromide, 1 mmon) in water (18 ml) was heated to get a solution. Thereafter, aralkyl chlorine (100 mmol) in 140 ml of benzene was added to the solution dropwise at 70° C., and refluxed for 1-3 h. The organic layer was washed with water and saline, dried (mgSO$_4$), filtered and evaporated, the residue was dissolved by 50 ml of ethanol and adjusted to PH=3 with HCl/$C_2H_5OH$, and the resulting precipitate was recrystallized from ethanol to obtain N-aralkyl piperazine dihydrochloride (55-86%).

General Preparation 2: $N^1$-aralkyl-$N^4$-arylformoxylalkyl piperazine dihydrochloride (III)

A mixture of N-aralkyl piperazine dihydrochloride (II) (10 mmol), halogenated aralkylketone (12 mmol), potassium iodide (1 mmol) and anhydrous $K_2CO_3$ (35 mmol) in DMF (50 ml) was stirred at 25° C.-50° C. for 8-12 hour, filtrated, and then evaporated to dryness, 50 ml of water was added to the residue, and extracted with EtOAc (100 ml×30). The combined organic layer was washed with saline, dried (mgSO$_4$). Filtered and evaporated, the residue was dissolved by 30 ml of ethanol and then adjusted to pH=2 with HCl/$C_2H_5OH$ (5N); the resulting precipitate was recrystallized from ethanol or $CH_3OH$ to obtain the title compound (III) (60-85%).

General Preparation 3: $N^1$-aralky-$N^4$-arylalkanol piperazine dihydrochloride (IV)

A mixture of $N^1$-aralkyl-$N^4$-arylformoxylalkyl piperazine dihydrochloride (III) (3.5 mmol) and $KHCO_3$ (8.75 mmol) in methanol (60 ml) was added $KBH_4$ (14 mmol), and stirred at room temperature for 2 h, and then refluxed for 3-5 hours. Adjusted to a PH of 8 by 1 N aqueous NaOH and then filtered. The filtrate was extracted with EtOAC (40 ml×30), washed with saline, evaporated to dryness, which was dissolved in 20 ml of ethanol, and adjusted to PH=2 with HCl/$C_2H_5OH$ (5N), the resulting precipitate was recrystallized from ethanol to obtain the title compound (60-80%).

Example 1

IV-1 $N^1$-benzyl-$N^4$-(phenylpropane-2-yl-3-ol) piperazine dihydrochloride

A mixture of N-benzylpiperazine dihydrochloride (7 mmol) and 2-bromo-1-phenylpropan-1-one (8.4 mmol) was treated according to the general preparation 2 to obtain $N^1$-benzyl-$N^4$-(1-benzoylethyl) piperazine dihydrochloride (2.6 g, 5 mmol), which was reduced according to the general preparation 3 to obtain 1.28 g of the title compound, yield 67%, mp 244-246° C.).

Elementary analysis: $C_{20}H_{26}N_2O\cdot 2HCl$. Found: (% C 62.68, H 7.49, N 7.18); theoretical value (% C 62.66, H 7.36, N 7.31).

IR (KCl): ν 3240, 2980, 1450, 1030

$^1$HNMR (DMSO-d$_6$): δ 0.99 (m, 3H, NCHCH$_2$), 3.44-3.92 (m, 9H, N—CH, piperazine-H), 4.40 (s, 2H, PhCH$_2$), 5.52 (br, 1H, PhCHOH), 7.24-7.67 (m, 10H, ArH).

MS: m/z 311, 221, 204

Example 2

IV-2 $N^1$-(4-chlorobenzyl)-$N^4$-(phenylpropane-2-yl-3-ol) piperazine dihydrochloride First of all, a mixture of 4-chlorobenzylchlorine and piperazine was treated according to the general preparation 1 to obtain N-(4-chlorobenzyl) piperazine dihydrochloride, yield 65%, mp 278-280° C. Then, a mixture of the above product (5 g, 20 mmol), $KHCO_3$ (70 mmol) and 2-bromo-1-phenylpropan-1-one (3.96 ml, 26 mmol) in 40 ml of ethanol was refluxed for 8 hours, and then treated according to the general preparation 2 to obtain 6.1 g of $N^1$-(4-chlorobenzyl)-$N^4$-(1-benzoylethyl) piperazine dihydrochloride, yield 59.51%, mp 260-262° C. Finally, a mixture of above compound (1.5 g, 3.45 mmol) and $KBH_4$ (0.74 g, 14 mmol) was treated according to the general preparation 3 to obtain the title compound, yield 65%, mp. 240° C.).

Elementary analysis: $C_{20}H_{25}ClN_2O\cdot 2HCl\cdot 2H_2O$. Found: (% C 54.74, H 6.71, N 6.34); theoretical value (% C 55.12, H 6.71, N 6.43).

MS: m/z 344 (M)$^+$

Example 3

IV-3 $N^1$-(1-phenylethyl)-$N^4$-(phenylpropane-2-yl-3-ol) piperazine dihydrochloride The $N^1$-(1-phenylethyl)-$N^4$-(1-benzoylethyl) piperazine (1.42 g, 3.5 mmol) could be prepared according to the general preparation 2, and then reduced according to the general preparation 3 to obtain 0.86 g of the title compound, yield 62%, mp. 232-233° C.).

Elementary analysis: $C_{21}H_{28}N_2O.2HCl$. Found: (% C 63.39, H 7.65, N 7.00); theoretical value (% C 63.47, H 7.61, N 7.05).

IR (KCl)° C. ν 3260, 2960, 1480, 1020

$^1$HNMR (DMSO-$d_6$): δ 0.97 (d, J=6.6, 3H, NCHCH$_3$), 1.72 (d, J=7.2, 3H, PhCHCH$_3$), 3.46-4.00 (m, 9H, N—CHCH$_3$, piperazine-H), 4.63 (br, 1H, PhCHN), 5.50 (br, 1H, PhCHOH), 7.23-7.67 (m, 10H, ArH).

MS: m/z 325 (M+H)$^+$ 221, 185

Example 4

IV-4 $N^1$-benzyl-$N^4$-[2-(4-chlorophenyl)ethyl-2-ol] piperazine dihydrochloride The $N^1$-benzyl-$N^4$-(4-chlorobenzoylmethyl) piperazine dihydrochloride (1.2 g, 3 mmol) could be prepared according to the general preparation 2, and then reduced according to the general preparation 3 to obtain 0.91 g of the title compound, yield 75%, mp. 240-242° C.).

Elementary analysis: $C_{19}H_{23}ClN_2O.2HCl$. Found: (% C 56.39, H 6.35, N 7.00); theoretical value (% C 56.52, H 6.24, N 6.94).

MS: m/z 331 (M$^+$)

Example 5

IV-5 $N^1$-(3-pyridylmethyl)-$N^4$-(2-phenylethyl-2-ol) piperazine trihydrochloride A mixture of 3-chloromethylpyridine and piperazine hexahydrate was treated according to the general preparation 1 to obtain N-(3-pyridylmethyl) piperazine trihydrochloride (62%). A mixture of the above product (3 mmol) and 2-chloro-1-phenylethanol (3.2 mmol) was treated according to the general preparation 2 to obtain the $N^1$-(3-pyridylmethyl)-$N^4$-phenacyl piperazine trihydrochloride (0.85 g, 2 mmol), which was reduced according to the general preparation 3 to obtain 0.61 g of the title compound, yield 72%, mp. 180-182° C.).

Elementary analysis: $C_{18}H_{23}N_3O.3HCl.H_2O$. Found: (% C 51.05, H 6.45, N 9.95); theoretical value (% C 50.92, H 6.65, N 9.89).

MS: m/z 297 (M$^+$)

Example 6

IV-6 $N^1$-(4-fluorobenzyl)-$N^4$-(2-phenylethyl-2-ol) piperazine dihydrochloride A mixture of 4-fluorobenzylchlorine and piperazine was treated according to the general preparation 1 to obtain N-(4-fluorobenzyl) piperazine dihydrochloride (67%), mp. 282-284° C. The $N^1$-(4-fluorobenzyl)-$N^4$-phenacyl piperazine dihydrochloride could be prepared according to the general preparation 2, which was reduced with KHCO$_3$ (0.65 g, 6.5 mmol) and KBH$_4$ (0.59 g, 10.4 mmol) in methanol (40 ml) according to the general preparation 3 to obtain 0.72 g of the title compound as white solid.

Elementary analysis: $C_{19}H_{23}FN_2O.2HCl$. Found: (% C 58.81, H 6.35, N 7.28); theoretical value (% C 58.92, H 6.51, N 7.23).

MS: m/z 314 (M$^+$)

Example 7

IV-7 $N^1$-benzyl-$N^4$-[2-(4-nitrophenyl)ethyl-2-ol] piperazine dihydrochloride The $N^1$-benzyl-$N^4$-(4-nitrophenacyl) piperazine dihydrochloride (0.84 g, 2 mmol) could be prepared according to the general preparation 2, and then reduced according to the general preparation 3 to obtain 0.60 g of the title compound, yield 70%, mp. 238-241° C.).

Elementary analysis: $C_{19}H_{23}N_3O_3.2HCl.½H_2O$. Found: (% C 54.05, H 6.25, N 9.85); theoretical value (% C 53.91, H 6.19, N 9.93).

MS: m/z 314 (M$^+$)

Example 8

IV-8 $N^1$-benzyl-$N^4$-[(1,2-diphenyl)ethyl-2-ol] piperazine dihydrochloride

The $N^1$-benzyl-$N^4$-(1-phenylbenzoylmethyl) piperazine dihydrochloride (2 g, 4.5 mmol) could be prepared according to the general preparation 2. A mixture of the above compound, KHCO$_3$ (10 mmol) and KBH$_4$ (10.4 mmol) in methanol (40 ml) was treated according to the general preparation 3 to obtain 1.2 g of the title compound as white solid, mp. 256-258° C.

Elementary analysis: $C_{25}H_{28}N_2O.2HCl.H_2O$. Found: (% C 65.04, H 6.80, N 5.67); theoretical value (% C 64.79, H 6.96, N 6.05).

MS: m/z 372 (M$^+$)

Example 9

IV-9 $N^1$-(4-nitrobenzyl)-$N^4$-[2-(4-acetamidophenyl) ethyl-2-ol] piperazine dihydrochloride A mixture of 4-nitrobenzylchlorine and piperazine was treated according to the general preparation 1 to obtain N-(4-nitrobenzyl) piperazine dihydrochloride, yield 64%, mp 242-244° C. The $N^1$-(4-nitrobenzyl)-$N^4$-[(4-acetamido) phenacyl] piperazine dihydrochloride (0.75 g, 1.5 mmol) could be prepared according to the general preparation 2, and then reduced according to the general preparation 3 to obtain 0.61 g of the title compound, yield 80%, mp 150-151° C.).

Elementary analysis: $C_{21}H_{26}N_4O_4.2HCl.2H_2O$. Found: (% C 49.55, H 6.25, N 11.15); theoretical value (% C 49.71, H 6.36, N 11.04).

MS: m/z 372 (M$^+$)

Example 10

IV-10 $N^1$-benzyl-$N^4$-[2-(4-acetamidophenyl)ethyl-2-ol] piperazine dihydrochloride The $N^1$-benzyl-$N^4$-[(4-acetamido) phenacyl] piperazine dihydrochloride could be synthesized according to the general preparation 2, and then reduced according to the general preparation 3 to obtain the title compound, yield 75%, mp 144-146° C.

Elementary analysis: $C_{21}H_{27}N_3O_2.2HCl.2H_2O$. Found: (% C 54.35, H 7.20, N 9.15); theoretical value (% C 54.54, H 7.19, N 9.08).

MS: m/z 353 (M$^+$)

Example 11

IV-11 $N^1$-(4-fluorobenzyl)-$N^4$-[2-(4-chlorophenyl)ethyl-2-ol] piperazine dihydrochloride The $N^1$-(4-fluorobenzyl)-$N^4$-(4-chlorophenacyl) piperazine dihydrochloride (0.87 g, 2 mmol) could be prepared according to the general preparation 2, and then reduced according to the general preparation 3 to obtain 0.65 g of the title compound, yield 76%, mp 236-238° C.).

Elementary analysis: $C_{19}H_{22}ClFN_2O·2HCl·½H_2O$. Found: (% C 53.05; H5.75, N6.65); theoretical value (% C 52.98, H 5.85, N 6.50).

MS: m/z 348 ($M^+$)

Example 12

IV-12 $N^1$-[1-(4-nitrophenyl)ethyl]-$N^4$-(2-phenylethyl-2-ol) piperazine dihydrochloride The $N^1$-[1-(4-nitrophenyl)ethyl]-$N^4$-phenacyl piperazine dihydrochloride was prepared according to the general preparation 2, and then reduced according to the general preparation 3 to obtain the the title compound, yield 76%, mp 220-222° C.

Elementary analysis: $C_{20}H_{25}N_3O_3·2HCl·H_2O$. Found: (% C 53.95, H 6.45, N 9.35); theoretical value (% C 53.81, H 6.55, N 9.41).

MS: m/z 355 ($M^+$)

Example 13

IV-13 $N^1$-(3-methoxybenzyl)-$N^4$-(2-phenylethyl-2-ol) piperazine dihydrochloride The $N^1$-(3-methoxybenzyl)-$N^4$-phenacyl piperazine (0.36 g, 1.1 mmol) could be prepared according to the general preparation 2. A mixture of above compound, $KHCO_3$ (0.28 g, 2.8 mmol) and $KBH_4$ (0.24 g, 4.4 mmol) in methanol (20 ml) was treated according to the general preparation 3 to obtain 0.24 g of the title compound as white solid.

Elementary analysis: $C_{20}H_{26}N_2O_2Cl·2HCl$. Found: (% C 60.31, H 6.93, N 7.14); theoretical value (% C 60.15, H 7.07, N 7.02).

MS: m/z 326 ($M^+$)

Example 14

IV-14 $N^1$-(2-nitro-5-methoxybenzyl)-$N^4$-(2-phenylethyl-2-ol)piperazine dihydro-chloride The $N^1$-(2-nitro-5-methoxybenzyl)-$N^4$-phenacyl piperazine dihydrochloride could be prepared according to the general preparation 2, and then reduced according to the general preparation 3 to obtain the title compound, yield 72%.

Elementary analysis: $C_{20}H_{25}N_3O_4·2HCl$. Found: (% C 53.98, H 6.25, N 9.35); theoretical value (% C 54.06, H 6.12, N 9.46).

MS: m/z 371 ($M^+$)

Example 15

IV-15 $N^1$-[1-(4-nitrophenyl)ethyl]-$N^4$-[2-(4-methylphenyl)ethyl-2-ol] piperazine dihydrochloride A mixture of $N^1$-[1-(4-nitrophenyl)ethyl]-$N^4$-(4-methylphenacyl) piperazine dihydrochloride (2 g, 4.54 mmol), $KHCO_3$ (1 g, 9.99 mmol) and $KBH_4$ (0.98 g, 18.17 mmol) in methanol (60 ml) was treated according to the general preparation 3 to obtain 1.54 g of the title compound as white solid.

Elementary analysis: $C_{21}H_{27}N_3O_3·2HCl$. Found: (% C 57.31, H 6.63, N 9.54); theoretical value (% C 57.01, H 6.61, N 9.50).

MS: m/z 369 ($M^+$)

Example 16

IV-16 $N^1$-benzyl-$N^4$-[2-(5-chloro-6-methoxy-2-naphthyl)ethyl-2-ol] piperazine dihydrochloride A mixture of N-benzylpiperazine dihydrochloride (2 g, 9.4 mmol), 2-bromo-1-(5-chloro-6-methoxynaphthalen-1-yl) ethanone (3.54 g, 11.3 mmol) and $K_2CO_3$ (4.55 g, 33 mmol) in acetone (120 ml) was treated according to the general preparation 2 to obtain $N^1$-benzyl-$N^4$-(5-chloro-6-methoxy-2-naphthoylmethyl) piperazine dihydro-chloride (2.85 g). The above product (2.6 g, 30 mmol) was reduced with $NaBH_4$ (2.22 g, 60 mmol) in methanol (150 ml) according to the general preparation 3 to obtain 10.2 g of the title compound as white solid.

Elementary analysis: $C_{24}H_{27}ClN_2O_2·2HCl$. Found: (% C 59.61, H 6.03, N 5.61); theoretical value (% C 59.65, H 6.05, N 5.80).

MS: m/z 410 ($M^+$)

Example 17

IV-17 $N^1$-(3-chlorophenyl)-$N^4$-[1-(5-chloro-6-methoxyl-naphthalen-2-yl)-propane-2-yl-1-ol] piperazine dihydrochloride A mixture of N-(3-chlorophenyl) piperazine dihydrochloride (1.35 g, 5 mmol), 2-bromo-1-(5-chloro-6-methoxynaphthalen-2-yl)propan-1-one (1.96 g, 6 mmol) and $K_2CO_3$ (2.42 g, 17.5 mmol) in DMF (40 ml) was treated according to the general preparation 2 to obtain 1.65 g of $N^1$-(3-chlorophenyl)-$N^4$-[1-(5-chloro-6-methoxy-2-naphthoyl)ethyl] piperazine dihydrochloride, yield 64%. The above product was reduced with $NaBH_4$ in methanol (50 ml) according to the general preparation 3 to obtain the title compound as white solid, yield 78%.

Elementary analysis: $C_{24}H_{26}Cl_2N_2O_2·2HCl$. Found: (% C 55.31, H 5.52, N 5.53); theoretical value (% C 55.61, H 5.45, N 5.41).

MS: m/z 445 ($M^+$)

Example 18

IV-18 $N^1$-(2-phenylethyl-2-ol)-$N^4$-[1-(5-chloro-6-methoxyl-naphthalen-2-yl)-propane-2-yl-1-ol] piperazine dihydrochloride The $N^1$-phenacyl-$N^4$-[1-(5-chloro-6-methoxy-2-naphthoyl)ethyl] piperazine di-hydrochloride could be prepared according to the general preparation 2, and then reduced according to the general preparation 3 to obtain the title compound, yield 70%.

Elementary analysis: $C_{26}H_{31}Cl N_2O_3·2HCl$. Found: (% C 59.31, H 6.09, N 5.41); theoretical value (% C 59.15, H 6.30, N 5.31).

MS: m/z 455 ($M^+$), 129, 111

Example 19

IV-19 $N^1$-benzyl-$N^4$-[1-(5-chloro-6-methoxyl-naphthalen-2-yl)-propane-2-yl-1-ol] piperazine dihydrochloride This compound has the formula as defined in claim 1, wherein $R_1$ is H, $R_2$ is $CH_3$; X is CHOH; $Ar_1$ is phenyl, $Ar_2$ is 5-chloro-6-methoxy-2-naphthyl; n=m=1.

A mixture of N-benzyl piperazine dihydrochloride (1.5 g, 7.05 mmol), 2-bromo-1-(5-chloro-6-methoxynaphthalen-2-yl) propan-1-one (2.8 g, 8.5 mmol) and triethyl-amine (2.38 g, 23.5 mmol) in benzene (150 ml) was treated according to the general preparation 2 to obtain 2.14 g of $N^1$-benzyl-$N^4$-[1-(5-chloro-6-methoxy-2-naphthoyl)ethyl] piperazine dihydrochloride, yield 60%, mp 252-253° C.).

To a mixture of the above product (1 g, 2 mmol) and $KHCO_3$ (0.5 g, 5 mmol) in methanol (50 ml) was added $KBH_4$ (0.44 g, 8 mmol), stirred at room temperature for 2 h, and then refluxed for 3 h, adjusted to pH=2 with 1 N aqueous NaOH and then filtered. The filtrate was extracted with EtOAC (40 ml×3), washed with saline, evaporated to dryness, which was dissolved in 20 ml of ethanol, and adjusted to pH=2 with $HCl/C_2H_5OH$. The resulting precipitate was recrystallized with ethanol (95%) to obtain the title compound, yield 75%. Content (HPLC): 99.80%.

Elementary analysis: $C_{25}H_{29}ClN_2O_3.2HCl$. Found: (% C 58.41, H 6.12, N 5.51); theoretical value (% C 58.43, H 6.08, N 5.45).

$^1$HNMR (DMSO-$d_6$): δ 0.97 (d, 3H, NCHCH$_3$), 2.81-2.93 (m, 9H, N—CHCH$_3$, piperazine-H), 4.02 (s, 3H, OCH$_3$), 5.32 (br, 1H, PhCHOH), 7.34-8.14 (m, 10H, ArH).

MS: m/z 425 (M+H)$^+$, 407

Example 20

IV-20   $N^1$-(4-nitrobenzyl)-$N^4$-[1-(5-chloro-6-methoxyl-naphthalen-2-yl)-propane-2-yl-1-ol] piperazine dihydrochloride The $N^1$-(4-nitrobenzyl)-$N^4$-[1-(5-chloro-6-methoxy-2-naphthoyl)ethyl] piperazine dihydrochloride (0.24 g, 0.5 mmol) could be prepared according to the general preparation 2, and then reduced with NaBH$_4$ (0.2 g, 5 mmol) in methanol (30 ml) according to the general preparation 3 to obtain 0.14 g of the title compound as white solid.

Elementary analysis: $C_{25}H_{28}Cl N_3O_4.2HCl$. Found: (% C 55.25, H 5.59, N 7.51); theoretical value (% C 55.31, H 5.57, N 7.74).

MS: m/z 470 (M$^+$)

Example 21

IV-21   $N^1$-(4-aminobenzyl)-$N^4$-[1-(5-chloro-6-methoxyl-naphthalen-2-yl)-propane-2-yl-1-ol] piperazine trihydrochloride A mixture of $N^1$-(4-aminobenzyl)-$N^4$-[1-(5-chloro-6-methoxy-2-naphthoyl)ethyl] piperazine trihydrochloride (0.08 g, 1.83 mmol) and NaBH$_4$ (0.1 g) in methanol (20 ml) was treated according to the general preparation 3 to obtain 0.05 g of the title compound as white solid.

Elementary analysis: $C_{25}H_{32}Cl N_3O_2.3HCl$. Found: (% C 54.31, H 6.53, N 7.54); theoretical value (% C 54.56, H 6.23, N 7.64).

MS: m/z 441 (M$^+$)

Example 22

IV-22   $N^1$-(3,4,5-trimethoxybenzyl)-$N^4$-[1-(5-chloro-6-methoxyl-naphthalen-2-yl)-propane-2-yl-1-ol] piperazine dihydrochloride A mixture of $N^1$-(3,4,5-trimethoxybenzyl)-$N^4$-[1-(5-chloro-6-methoxy-2-naphthoyl)ethyl] piperazine dihydrochloride (0.8 g, 1.4 mmol) and NaBH$_4$ (0.155 g, 4.1 mmol) in methanol (20 ml) was treated according to the general preparation 3 to obtain 0.19 g of the title compound as white solid, mp: 226-228° C.

Elementary analysis: $C_{28}H_{35}Cl N_2O_5.2HCl$. Found: (% C 57.31, H 6.63, N 4.54); theoretical value (% C 57.20, H 6.34, N 4.77).

MS: m/z 541 (M$^+$)

Example 23

IV-23   $N^1$-(4-methoxybenzyl)-$N^4$-(2-phenylethyl-2-ol) piperazine dihydrochloride A mixture of 4-methoxybenzylchlorine and piperazine was treated according to the general preparation 1 to obtain N-(4-methoxybenzyl) piperazine dihydrochloride, yield 75%, mp. 250-252° C. The $N^1$-(4-methoxybenzyl)-$N^4$-phenacyl piperazine dihydrochloride (0.5 g, 1.23 mmol) could be prepared according to the general preparation 2, and then reduced according to the general preparation 3 to obtain 0.38 g of the title compound, yield 77.55%, mp 244-246° C.).

Elementary analysis: $C_{20}H_{26}N_2O_2.2HCl$. Found: (% C 59.84, H 7.04, N 6.83); theoretical value (% C 60.15, H 7.07, N 7.02).

IR (KCl): v 3340, 2980, 1620, 1040

MS: m/z 327 (M+H)$^+$, 208, 185

Example 24

IV-24   $N^1$-(4-methoxybenzyl)-$N^4$-(S-2-phenylethyl-2-ol) piperazine dihydrochloride A solution of S-(+)-mandelic acid (10 mmol) in acetylchloride (30 mmol), was stirred at 25° C. for 12 hours, and then evaporated to dryness. The residue was dissolved in DMF (20 ml) and then added N-ethyl-N-isopropylpropan-2-amine (11 mmol) and $C_2H_5O_2CC$ (CN)=NOC [N(CH$_3$)$_2$]=N(CH$_3$)$_2$ BF$_4$ (11 mmol) at 0° C. under N$_2$, stirred at the same temperature for 1 hour. After the addition of N-(4-methoxybenzyl) piperazine (10 mmol), the reaction mixture was stirred at 25° C. for 24 hours. and then evaporated to dryness, which was diluted in water (20 ml) and chloroform (50 ml). The organic phase was washed with water, NaHCO$_3$, 5% citric acid and saline (10 ml), dried (mgSO$_4$), filtered and then evaporated to obtain $N^1$-(4-methoxybenzyl)-$N^4$-(1-oxo-S-2-phenylethyl-2-ol) piperazine as oil, directly used in the next step.

A mixture of above compound (50 mmol) and LiAlH$_4$ (125 mmol) in THF (150 ml) was refluxed for 2 hours, added Na$_2$SO$_4$ (6 g), and then stirred for 1 hour. After filtration, the filtrate was adjusted to pH=2 with HCl/C$_2$H$_5$OH, the resulting precipitate was recrystallized with ethanol to obtain the title compound, yield 75%, mp 223-224° C. $[\alpha]_D^{20}$+12.9 (c 1, H$_2$O).

Elementary analysis: $C_{20}H_{26}N_2O_2.2HCl$. Found: (% C 60.23, H 7.11, N 6.61); theoretical value (% C 60.15, H 7.07, N 7.02).

$^1$HNMR (DMSO-$d_6$): 3.57 (m, 10H, NCH$_2$, piperazine-H), 3.77 (s, 3H, OCH$_3$), 4.34 (s, 2H, PHCH$_2$), 5.14 (m, 1H, PhCHOH), 6.99-7.59 (m, 9H, ArH).

MS: m/z 327 (M+H)$^+$, 207

Example 25

IV-25   $N^1$-(4-methoxybenzyl)-$N^4$-(R-2-phenylethyl-2-ol) piperazine dihydrochloride Using R-(−)-mandelic acid and N-(4-methoxybenzyl) piperazine in the similar procedure of example 24 to obtain the title compound, mp 238-239° C., $[\alpha]_D^{20}$−13.1 (c 1, H$_2$O).

Elementary analysis: $C_{20}H_{26}N_2O_2.2HCl$. Found: (% C 60.34, H 7.17, N 6.58); theoretical value (% C 60.15, H 7.07, N 7.02).

¹HNMR (DMSO-d₆): δ 3.52 (m, 10H, NCH₂, piperazine-H), 3.77 (s, 3H, OCH₃), 4.33 (s, 2H, PHCH₂), 5.14 (t, 1H, PhCHOH), 6.99-7.59 (m, 9H, ArH).

MS: m/z 327 (M+H)⁺, 207, 185

Example 26

IV-26 N¹-(4-nitrobenzyl)-N⁴-(2-phenylethyl-2-ol) piperazine dihydrochloride

The N¹-(4-nitrobenzyl)-N⁴-phenacyl piperazine dihydrochloride (0.5 g, 1.21 mmol) could be prepared according to the general preparation 2, and then reduced according to the general preparation 3 to obtain 0.3 g of the title compound, mp 242-243° C.).

Elementary analysis: $C_{19}H_{23}N_3O_3 \cdot 2HCl \cdot \frac{1}{2}H_2O$. Found: (% C 53.84, H 6.04, N 10.03); theoretical value (% C 53.90, H 6.19, N 9.93).

MS: m/z 342 (M+H)⁺

Example 27

IV-27 N¹-(4-nitrobenzyl)-N⁴-(S-2-phenylethyl-2-ol) piperazine dihydrochloride

Using S-(+)-mandelic acid (22 mmol) and N-benzylpiperazine (20 mmol) as starting materials to prepare N¹-benzyl-N⁴-(S-2-phenylethyl-2-ol)piperazine dihydrochloride in the similar procedure of example 24.

A mixture of the above product (1.8 g, 4.88 mmol) and 10% Pd—C (0.2 g) in HAc (40 ml) was passed hydrogen at 70% for 3 hours, and filtered then evaporated to dryness. The residue was dissolved in ethanol (20 ml), adjusted solution to pH=2 with HCl/C₂H₅OH, recrystallized with ethanol (95%) to obtain 1.14 g of N-(2S-phenylethyl-2-ol) piperazine dihydrochloride, yield 85%.

A mixture of N-(S-2-phenylethyl-2-ol) piperazine dihydrochloride (4.1 mmol) and 4-nitrobenzylchlorine (0.77 g, 4.49 mmol) was treated according to the general preparation 2 to obtain the title compound, yield 47%, mp. 214-216° C. $[\alpha]_D^{20}$+14.0 (c 1, H₂O).

Elementary analysis: $C_{19}H_{23}N_3O_3 \cdot 2HCl \cdot 1H_2O$. Found: (% C 53.02, H 5.93, N 7.69); theoretical value (% C 52.78, H 6.29, N 7.72).

¹HNMR (DMSO-d₆): δ3.52-3.80 (br, 10H, NCH₂, piperazine-H), 4.49 (s, 2H, PHCH₂), 5.14 (m, 1H, PhCHOH), 7.28-8.32 (m, 9H, ArH).

MS: m/z 342 (M+H)⁺, 185

Example 28

IV-28 N¹-(4-nitrobenzyl)-N⁴-(R-2-phenylethyl-2-ol) piperazine dihydrochloride

Using R-(−)-mandelic acid and N-benzyl piperazine as starting materials to prepare N-(R-2-phenylethyl-2-ol) piperazine dihydrochloride in the similar procedure of example 27. A mixture of the above compound and 4-nitrobenzylchlorine was treated according to the general preparation 2 to obtain the title compound, yield 48%, mp 239-241° C. $[\alpha]_D^{20}$ −7.1 (c 1, H₂O).

Elementary analysis: $C_{19}H_{23}N_3O_3 \cdot 2HCl$. Found: (% C 54.66, H 6.06, N 10.09); theoretical value (% C 55.08, H 6.08, N 10.14).

¹HNMR (DMSO-d₆): δ 3.52 (br, 10H, NCH₂, piperazine-H), 4.48 (s, 2H, PHCH₂), 5.14 (t, 1H, PhCHOH), 7.28-8.31 (m, 9H, ArH).

MS: m/z 342 (M+H)⁺, 207, 185

Example 29

IV-29 N¹-(1-phenylethyl)-N⁴-(2-phenylethyl-2-ol) piperazine dihydrochloride

Using N¹-(1-phenylethyl)-N⁴-phenacyl piperazine (IIV-37) (1.5 g, 3.9 mmol) as a starting material, and then reduced according to the general preparation 3 to obtain 1 g of the title compound, mp 254-255° C.).

Elementary analysis: $C_{20}H_{26}N_2O \cdot 2HCl$. Found: (% C 62.43, H 7.38, N 7.18); theoretical value (% C 62.66, H 7.36, N 7.31).

MS: m/z 310 (M⁺)

Example 30

IV-30 N¹-(R-1-phenethyl)-N⁴-(R-2-phenylethyl-2-ol) piperazine dihydrochloride (1) N-(R-1-phenethyl) piperazine dihydrochloride A mixture of chloroacetic acid (94.5 g) and 32.2 ml of R-1-phenylethylamine in 125 ml of 8N NaOH was reacted at 70□ for 10 hours, and added a solution of BaCl₂ (65 g) in 200 ml of water dropwise, and then refluxed for 1 hour. After filtration, the solid was put into 400 ml of water and then added 100 ml of 5N H₂SO₄, refluxed for 1 hour, filtered and washed with water, the filtrate was evaporated in vacuo to give N,N-di(hydroxyformyl)-(R)-1-phenylethylamine.

A mixture of the above product and 80 ml of formamide in 80 ml of Xylene was refluxed for 8 hours, and then extracted with EtOAC (100 ml×2). The combined organic layer was washed with water, concentrated in vacuo to obtain (R)-4-(1-phenylethyl) piperazine-2,6-dione as colorless crystals. Yield 72% (two steps).

A mixture of (R)-4-(1-phenylethyl)piperazine-2,6-dione (10.9 g, 50 mmol) and LiAlH₄ (4.75 g, 125 mmol) in 150 ml of THF was refluxed for 2 hours, and then added Na₂SO₄ (6 g), stirred for 1 hour, filtered and washed with EtOAC, the filtrate was adjusted to pH=2 with HCl/C₂H₅OH. The resulting precipitate was recrystallized from ethanol to give N-(R-1-phenylethyl) piperazine dihydrochloride, yield 85%. $[\alpha]_D^{20}$+22.40° (c=1, MeOH). MS: m/z 190 (M⁺).

(2) Using the above product (10 mmol) and R-(−)-mandelic acid (12 mmol) in the similar procedure of example 24 to obtain the title compound, mp 247-248° C., $[\alpha]_D^{20}$−18.58 (c 1, CH₃OH).

Elementary analysis: $C_{20}H_{26}N_2O \cdot 2HCl$. Found: (% C 62.95, H 7.50, N 7.23); theoretical value (% C 62.66, H 7.36, N 7.31).

IR (KBr): 3260, 2970, 1460, 760, 710 cm⁻¹.

¹HNMR (DMSO-d₆): δ 1.76-1.78 (d, 3H, CH₃), 3.39-3.70 (m, 10H, NCH₂, piperazine-H), 4.55-4.61 (m, 1H, NCH), 5.13-5.16 (m, 1H, PhCHOH), 7.37-8.53 (m, 10H, ArH)

MS: m/z 311 (M+H)⁺, 207, 191, 103

Example 31

IV-31 N¹-(R-1-phenylethyl)-N⁴-(S-2-phenylethyl-2-ol) piperazine dihydrochloride

Using N-(R-1-phenethyl) piperazine (10 mmol) and S-(+)-mandelic acid (12 mmol) in the similar procedure of example 24 to obtain the title compound, mp 242-244° C., $[\alpha]_D^{20}$+ 48.72 (c 1, CH₃OH).

Elementary analysis: $C_{20}H_{26}N_2O \cdot 2HCl$. Found: (% C 62.75, H 7.60, N 7.43); theoretical value (% C 62.66, H 7.36, N 7.31).

IR (KBr): 3260, 2980, 1440, 760, 710 cm⁻¹

¹HNMR (DMSO-d₆): δ 1.76-1.78 (d, 3H, CH₃), 3.40-3.73 (m, 10H, NCH₂, piperazine-H), 4.56-4.61 (m, 1H, NCH), 5.12-5.15 (m, 1H, PhCHOH), 7.38-8.53 (m, 10H, ArH)

MS: m/z 311 (M+H)⁺, 207, 191, 103

Example 32

IV-32 N¹-(S-1-phenethyl)-N⁴-(S-2-phenylethyl-2-ol) piperazine dihydrochloride

Using (S)-phenylethyla mine as a starting material to prepare N¹-(S-1-phenethyl) piperazine dihydrochloride in the similar procedure of example 30, $[\alpha]_D^{20}$ –22.50° (c=1, MeOH). The above product (10 mmol) was reacted with S-(+)-mandelic acid (12 mmol) in the similar procedure of example 24 to obtain the title compound, mp 247-248☐, $[\alpha]_D^{20}$ +18.21 (c 1, CH₃OH).

Elementary analysis: C₂₀H₂₆N₂O.2HCl. Found: (% C 62.38, H 7.41, N 7.24); theoretical value (% C 62.66, H 7.36, N 7.31).

IR (KBr): 3260, 2985, 1450, 760, 710 cm⁻¹.

¹HNMR (DMSO-d₆): δ 1.76-1.78 (d, 3H, CH₃), 3.38-3.69 (m, 10H, NCH₂, piperazine-H), 4.56-4.61 (m, 1H, NCH), 5.12-5.15 (m, 1H, PhCHOH), 7.37-8.53 (m, 10H, ArH)

MS: m/z 311 (M+H)⁺, 207, 191, 103

Example 33

IV-33 N¹-(S-1-phenethyl)-N⁴-(R-2-phenylethyl-2-ol) piperazine dihydrochloride

Using R-(−)-mandelic acid (12 mmol) and N-(S-1-phenethyl) piperazine (10 mmol) in the similar procedure of example 24 to obtain the title compound, mp 230-232° C., $[\alpha]_D^{20}$ –48.42 (c 1, CH₃OH).

Elementary analysis: C₂₀H₂₆N₂O.2HCl. Found: (% C 62.50, H 7.49, N 7.44); theoretical value (% C 62.66, H 7.36, N 7.31).

IR (KBr): 3260, 2985, 1450, 760, 710 cm⁻¹.

¹HNMR (D₂O): δ 1.76-1.78 (d, 3H, CH₃), 3.40-3.73 (m, 10H, NCH₂, piperazine-H), 4.56-4.61 (m, 1H, NCH), 5.12-5.15 (m, 1H, PhCHOH), 7.37-8.53 (m, 10H, ArH)

MS: m/z 311 (M+H)⁺, 207, 191, 103

Example 34

IV-34 N¹-(S-1-phenylethyl)-N⁴-[1-(5-chloro-6-methoxyl-naphthalen-2-yl)-propane-2-yl-1-ol] piperazine dihydrochloride A mixture of N¹-(S-1-phenylethyl)-N⁴-[1-(5-chloro-6-methoxy-2-naphthoyl)ethyl] piperazine dihydrochloride (2.55 g, 5 mmol) and NaBH₄ (1.9 g, 51 mmol) in methanol (20 ml) was treated according to the general preparation 3 to obtain 1.2 g of the title compound as white solid.

Elementary analysis: C₂₆H₃₁ClN₂O₅.2HCl. Experimental: (% C 61.21, H 6.63, N 5.54); theoretical value (% C 61.00, H 6.50, N 5.47).

MS: m/z 439 (M+H)⁺

Example 35

IV-35 N¹-(R-1-phenylethyl)-N⁴-[1-(5-chloro-6-methoxyl-naphthalen-2-yl)-propane-2-yl-1-ol] piperazine dihydrochloride The title compound was prepared by using N¹-(R-1-phenylethyl)-N⁴-[1-(5-chloro-6-methoxy-2-naphthoyl)ethyl] piperazine dihydrochloride (2.55 g, 5 mmol) in the similar procedure of example 34.

Example 36

| | |
|---|---|
| Tablet: The compound in this invitation | 10 mg |
| Sucrose | 150 mg |
| Corn starch | 38 mg |
| Calcium stearate | 2 mg |

Preparation: A mixture of the active constituent, sucrose and corn starch in water was well stirred, and then dried and sifted, which was mixed with Calcium stearate evenly, and tableted. Each tablet is 200 mg containing 10 mg of the active compound.

Example 37

| | |
|---|---|
| Injection: The compound in this invitation | 20 mg |
| Physiological saline | 80 mg |

Preparation: The active constituent was dissolved in physiological saline, and then mixed evenly and filtered. The obtained clear solution was filled separately into ampoules under the aseptic condition, and the composition of each ampoule is weight of 10 mg, which containing 2 mg of the active compound.

Example 38

Antidepressant Effect of the Compounds

1. Inhibitory effects of compounds on uptaking serotonin (5-HT) and noradrenaline (NA) by brain synaptosomes:

The trial of uptaking the mono-amines neurotransmitter by synaptosomes is now one of the common method to study the central nervous pharmacology. This method is not only used to study the action mechanism of the medicament, but also to look for new antidepressant drugs which act on this tache. This method is used in the present invention, and selected Fluoxetine which is an inhibitor of 5-HT uptake and Desipra mine which is an inhibitor of NA uptake as control drugs to study the effects of invented compounds for inhibiting uptake of 5-HT and NA by brain synaptosomes. The method is recounted as follows:

(1). Preparation of synaptosomes. According to the described method by literatures (a. Biochem Pharmacol 1973, 22: 311-322, b. Methods in Neurochemistry, Vol. 2, New York: Marcel Dakker, Inc, 1972, 1-52), rats were decapitated, the brains rapidly excised, and frontal cortex dissected out on ice-cold saline (4° C.). The 3 g tissue was homogenized in 30 ml of ice-cold 0.32M sucrose and then centrifuged (1500 g) for 10 min (4° C.). The pellet was discarded and the supernatant centrifuged (20000 g) for 30 min (4° C.). After refined, the pellet was resuspended in buffer and immediately used. Protein content was deter mined with kit of total protein.

(2). Uptake of 5-HT. According to the described method by literatures (Br J Pharmacol, 1997, 122: 302-306; b. 1992, 105: 147-151), in the tubes, 1.0 ml artificial cerebral fluid, 20 μl suspension of synaptosomes and 10 μl solution of compound were added. After mixing, the tubes were incubated 5 min in 37° C. Uptake was started by addition of 10 μl [³H]-5-HT or [³H]-NA (300 nM), after another mixing, the tubes were incubated again 5 min in 37° C. The reaction was stopped by cooling the tubes in ice, the samples were then filtered through glass fibre filters and washed twice with artificial cerebral fluid. After drying in 60-70° C., the filter membranes were put into scintillation tubes. Filter-bound radioactivity was counted by scintillation spectrometry. The difference in [³H]-5-HT or [³H]-NA at 37° C. and 0° C. was taken as a measure of active uptake.

(3). Results: Under the same concentration (0.1 mmol/L for Fluoxetine and compounds), inhibited ratios of uptake 5-HT by Fluoxetine, and of uptake NA by Desipra mine count 100%, the results were setting out in Table 3.

TABLE 3

Inhibitive Effects of Compounds on Brain Synaptosome Uptake of 5-HT and NA

| Compounds | Inhibited ratio of uptake for 5-HT(%) | Inhibited ratio of uptake for NA(%) |
|---|---|---|
| IV-2 | 82 | 62 |
| IV-4 | 85 | 51 |
| IV-6 | 79 | 107 |
| IV-8 | <10 | 104 |
| IV-11 | 81 | 101 |
| IV-17 | 99 | 30 |
| IV-18 | 127 | 23 |
| IV-19 | 114 | 140 |
| IV-20 | 110 | 108 |
| IV-22 | 116 | 77 |
| IV-26 | 63 | 80 |
| IV-34 | 108 | 10 |
| IV-35 | 107 | 58 |
| Fluoxetine | 100 | |
| Desipra mine | | 100 |

Using the tail suspension test of "behavioural despair" and the mouse forced swimming test, and choosing Desipra mine as control medicament, to study the primary antidepressant effect of IV-19 that has the strong inhibited effect for both uptake of 5-HT and NA. The results are as follows:

(1). In the tail suspension test, IV-19 can diminish obviously the immobile times of mouse due to despair. The effect induced by 50 mg/kg IV-19 (20.2±16.05 sec) is the same as 10 mg/kg Desipra mine (27.5±21.93 sec), but a significant difference occurs when comparing with control (89.7±38.27).

(2). In the mouse forced swimming test, IV-19 also can diminish obviously the immobile times of mouse in water due to despair. As the results of tail suspension test, the effect induced by 50 mg/kg IV-19 (46.3±30.2 sec) is the same as 10 mg/kg Desipra mine (46±27.36 sec), but a significant difference occurs when comparing with control (93.4±27.36).

3. Acute toxicity:

$LD_{50}$ of VI-19 (p.o. in mice) is about 1 g/kg calculated with Bliss.

4. Bacterial reverse-mutation assay (Ames TS) of IV-19

*Bacillus: S. Typhimurium* $TA_{97}$, $TA_{98}$, $TA_{100}$ and $TA_{102}$

Results: The assay includes two parts of without $S_9$ and with $S_9$, in the system without $S_9$ $TA_{98}$ 5000 μg/utensil, and with $S_9$ $TA_{97}$ 5000 μg/utensil have the inhibitory effect for the growth of bacterial. The other doses haven't inhibitory effect for all bacteria, the growth of bacteria is well. All tested doses didn't induce the evident increase of revertants, Ames TS of V-19 is negative.

What we claim is:

1. A compound of formula I:

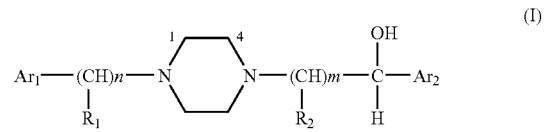

(I)

wherein $Ar_1$ and $Ar_2$ independently represent:

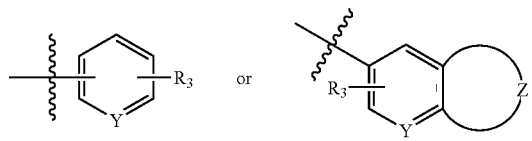

$R_1$, $R_2$ and $R_3$ each represents hydrogen, a $C_1$-$C_3$ alkyl group, a $C_5$ or $C_6$ cycloalkyl group, a phenyl, substituted phenyl, methoxy, ethoxy, amino, substituted amino, halogen, carboxylic acid, carboxylic ester, nitryl or acetonitrile group;

Y represents C, N, or O;

Z represents a five or six-member carbocyclic ring, or a five or six-member heterocyclic ring where at least one carbon is replaced by S, N or O;

n represents 1, 2 or 3;

m represents 1, 2 or 3;

in the form of a free base or a salt thereof.

2. A compound according to claim 1, wherein the salt is selected from the group consisting of hydrochloride, hydrobromide, sulfate, trifluoroacetate and methanesulfonate.

3. A compound according to claim 2, wherein the salt is hydrochloride or hydrobromide.

4. A compound according to claim 2, wherein the salt comprises about 0.5-3 molecules of hydrate water.

5. A compound according to claim 1, wherein $R_1$, $R_2$ and $R_3$ represents independently of each other hydrogen, a $C_1$-$C_3$ alkyl, methoxy, ethoxy, amino, substituted amino, halogen, or nitryl group.

6. A compound according to claim 1, in the form of a racemic mixture.

7. A compound according to claim 1, in the form of a pure enantiomer, or a mixture of enantiomers in a non-racemic ratio.

8. The compound of claim 1, selected from the group consisting of:

| | |
|---|---|
| IV-1 | $N^1$-benzyl-$N^4$-(phenylpropane-2-yl-3-ol)piperazine, |
| IV-2 | $N^1$-(4-chlorobenzyl)-$N^4$-(phenylpropane-2-yl-3 -ol)piperazine, |
| IV-3 | $N^1$-(1-phenylethyl)-$N^4$-(phenylpropane-2-yl-3 -ol)piperazine, |
| IV-4 | $N^1$-benzyl-$N^4$-[2-(4-chlorophenyl)ethyl-2-ol]piperazine, |
| IV-5 | $N^1$-(3-pyridylmethyl)-$N^4$-(2-phenylethyl-2-ol)piperazine, |
| IV-6 | $N^1$-(4-fluorobenzyl)-$N^4$-(2-phenylethyl-2-ol)piperazine, |
| IV-7 | $N^1$-benzyl-$N^4$-[2-(4-nitrophenyl)ethyl-2-ol]piperazine, |
| IV-8 | $N^1$-benzyl-$N^4$-[(1,2-diphenyl)ethyl-2-ol]piperazine, |
| IV-9 | $N^1$-(4-nitrobenzyl)-$N^4$-[2-(4-acetamidophenyl)ethyl-2- ol]piperazine, |
| IV-10 | $N^1$-benzyl-$N^4$-[2-(4-acetamidophenyl)ethyl-2- ol]piperazine, |
| IV-11 | $N^1$-(4-fluorobenzyl)-$N^4$-[2-(4-chlorophenyl)ethyl-2- ol]piperazine, |

| | |
|---|---|
| IV-12 | $N^1$-[1-(4-nitrophenyl)ethyl]-$N^4$-(2-phenylethyl-2-ol)piperazine, |
| IV-13 | $N^1$-(3-methoxybenzyl)-$N^4$-(2-phenylethyl-2-ol)piperazine, |
| IV-14 | $N^1$-(2-nitro-5-methoxybenzyl)-$N^4$-(2-phenylethyl-2-ol)piperazine, |
| IV-15 | $N^1$-[1-(4-nitrophenyl)ethyl]-$N^4$-[2-(4-methylphenyl)ethyl-2-ol]piperazine, |
| IV-16 | $N^1$-benzyl-$N^4$-[2-(5-chloro-6-methoxy-2-naphthyl)ethyl-2-ol]piperazine, |
| IV-17 | $N^1$-(3-chlorophenyl)-$N^4$-[1-(5-chloro-6-methoxyl-naphthalen-2-yl)-propane-2-yl-1-ol]piperazine, |
| IV-18 | $N^1$-(2-phenylethyl-2-ol)-$N^4$-[1-(5-chloro-6-methoxyl-naphthalen-2-yl)-propane-2-yl-1-ol]piperazine, |
| IV-19 | $N^1$-benzyl-$N^4$-[1-(5-chloro-6-methoxyl-naphthalen-2-yl)-propane-2-yl-1-ol]piperazine, |
| IV-20 | $N^1$-(4-nitrobenzyl)-$N^4$-[1-(5-chloro-6-methoxyl-naphthalen-2-yl)-propane-2-yl-1-ol]piperazine, |
| IV-21 | $N^1$-(4-aminobenzyl)-$N^4$-[1-(5-chloro-6-methoxyl-naphthalen-2-yl)-propane-2-yl-1-ol]piperazine, |
| IV-22 | $N^1$-(3,4,5-trimethoxybenzyl)-$N^4$-[1-(5-chloro-6-methoxyl-naphthalen-2-yl)-propane-2-yl-1-ol]piperazine, |
| IV-23 | $N^1$-(4-methoxybenzyl)-$N^4$-(2-phenylethyl-2-ol)piperazine, |
| IV-24 | $N^1$-(4-methoxybenzyl)-$N^4$-(S-2-phenylethyl-2-ol)piperazine, |
| IV-25 | $N^1$-(4-methoxybenzyl)-$N^4$-(R-2-phenylethyl-2-ol)piperazine, |
| IV-26 | $N^1$-(4-nitrobenzyl)-$N^4$-(2-phenylethyl-2-ol)piperazine, |
| IV-27 | $N^1$-(4-nitrobenzyl)-$N^4$-(S-2-phenylethyl-2-ol)piperazine, |
| IV-28 | $N^1$-(4-nitrobenzyl)-$N^4$-(R-2-phenylethyl-2-ol)piperazine, |
| IV-29 | $N^1$-(1-phenylethyl)-$N^4$-(2-phenylethyl-2-ol)piperazine, |
| IV-30 | $N^1$-(R-1-phenylethyl)-$N^4$-(R-2-phenylethyl-2-ol)piperazine, |
| IV-31 | $N^1$-(R-1-phenylethyl)-$N^4$-(S-2-phenylethyl-2-ol)piperazine, |
| IV-32 | $N^1$-(S-1-phenylethyl)-$N^4$-(S-2-phenylethyl-2-ol)piperazine, |
| IV-33 | $N^1$-(S-1-phenylethyl)-$N^4$-(R-2-phenylethyl-2-ol)piperazine, |
| IV-34 | $N^1$-(S-1-phenylethyl)-$N^4$-[1-(5-chloro-6-methoxyl-naphthalen-2-yl)-propane-2-yl-1-ol]piperazine, |
| IV-35 | $N^1$-(R-1-phenylethyl)-$N^4$-[1-(5-chloro-6-methoxyl-naphthalen-2-yl)-propane-2-yl-1-ol]piperazine, |
| IV-36 | $N^1$-benzyl-$N^4$-(2-phenylethyl-2-ol)piperazine, |
| IV-37 | $N^1$-(4-chlorobenzyl)-$N^4$-(2-phenylethyl-2-ol)piperazine, |
| IV-38 | $N^1$-(4-chlorobenzyl)-$N^4$-[2-(4-chlorophenyl)ethyl-2-ol]piperazine, |
| IV-39 | $N^1$-benzyl-$N^4$-[2-(4-methoxyphenyl)ethyl-2-ol]piperazine, |
| IV-40 | $N^1,N^4$-di(2-phenylethyl-2-ol)-piperazine, |
| IV-41 | $N^1$-(4-aminobenzyl)-$N^4$-(2-phenylethyl-2-ol)piperazine, |
| IV-42 | $N^1$-benzyl-$N^4$-[(2-naphthyl)ethyl-2-ol]piperazine, |
| IV-43 | $N^1$-benzyl-$N^4$-[(3-phenyl)propyl-3-ol]piperazine, |
| IV-44 | $N^1$-(2,4-dimethoxybenzyl)-$N^4$-(2-phenylethyl-2-ol)piperazine, |
| IV-45 | $N^1$-benzyl-$N^4$-(S-2-phenylethyl-2-ol)piperazine, |
| IV-46 | $N^1$-benzyl-$N^4$-(R-2-phenylethyl-2-ol)piperazine, |
| IV-47 | $N^1$-(1-phenylpropyl)-$N^4$-(2-phenylethyl-2-ol)piperazine, |
| IV-48 | $N^1$-(4-fluorobenzyl)-$N^4$-(2-phenylethyl-2-ol)piperazine, |
| IV-49 | $N^1$-(3,4-methylenedioxybenzyl)-$N^4$-(2-phenylethyl-2-ol)piperazine, |
| IV-50 | $N^1$-(1-phenethyl)-$N^4$-[2-(4-methylphenyl)ethyl-2-ol]piperazine, |
| IV-51 | $N^1$-(S-1-phenylethyl)-$N^4$-[2-(4-methylphenyl)ethyl-2-ol]piperazine, and |
| IV-52 | $N^1$-(R-1-phenethyl)-$N^4$-[2-(4-methylphenyl)ethyl-2-ol]piperazine. |

9. The compound according to claim 7, which is $N^1$-benzyl-$N^4$-[1-(5-chloro-6-methoxyl-naphthalen-2-yl)-propane-2-yl-1-ol]piperazine.

10. A pharmaceutical composition comprising a compound of claim 1, and a pharmaceutically acceptable excipient.

11. A method for treating depression, the method comprising administering to a patient in need thereof an effective amount of the pharmaceutical composition according to claim 10.

* * * * *

UNITED STATES PATENT AND TRADEMARK OFFICE
CERTIFICATE OF CORRECTION

| | |
|---|---|
| PATENT NO. | : 7,576,086 B2 |
| APPLICATION NO. | : 10/516205 |
| DATED | : August 18, 2009 |
| INVENTOR(S) | : Li et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this

Seventh Day of September, 2010

David J. Kappos
*Director of the United States Patent and Trademark Office*